United States Patent [19]

Pickens

[11] 4,133,834

[45] Jan. 9, 1979

[54] PROCESS FOR PREPARING α- AND β-HYDROXY OXIMES

[75] Inventor: Donald Pickens, Mendham, N.J.

[73] Assignee: Allied Chemical Corporation, Morris Township, Morris County, N.J.

[21] Appl. No.: 866,421

[22] Filed: Jan. 3, 1978

[51] Int. Cl.$^2$ .......................................... C07C 131/00
[52] U.S. Cl. ................................................ 260/566 A
[58] Field of Search ................................. 260/566 A

[56] References Cited

U.S. PATENT DOCUMENTS

| | | | |
|---|---|---|---|
| 3,592,775 | 7/1971 | Swanson | 260/566 A |
| 3,808,275 | 4/1974 | Hirose et al. | 260/566 A |

*Primary Examiner*—Gerald A. Schwartz
*Attorney, Agent, or Firm*—Alan M. Doernberg; Jay P. Friedenson; Henry E. Naylor

[57] ABSTRACT

An improved process is disclosed for preparing α-and β-hydroxy oximes wherein said oximes are prepared in the presence of a water soluble compound capable of contributing ferric or ferrous ions to the reaction medium. Such oximes are useful as metal complexing agents. Such complexing agents are used in processes of extracting metals from an ore solution.

20 Claims, No Drawings

PROCESS FOR PREPARING α- AND β-HYDROXY OXIMES

BACKGROUND OF THE INVENTION

Field of the Invention

This invention relates to the use of catalytic amounts of $Fe^{+2}$ and $Fe^{+3}$ contributing compounds for preparing α-and β-hydroxy oximes.

Description of the Prior Art

α- and β-hydroxy oximes are well-known in the art and are generally used for extracting metals such as copper, cobalt and nickel from aqueous metal ore solutions. Several methods for preparing these oximes are known in the art. For example, U.S. Pat. No. 3,449,066 describes a process for preparing aliphatic α-hydroxy oximes wherein the corresponding acyloin is reacted with a hydroxylamine salt under reflux conditions in an alcohol medium such as methanol. The reaction must be neutralized with a salt of a weak base such as anhydrous sodium acetate.

The β-hydroxy oximes are generally aromatic in structure and are usually prepared by reacting the corresponding phenone with a hydroxylamine salt under reflux conditions in an alcohol medium and in the presence of a weak base such as anhydrous sodium acetate. Exemplary processes of this type are disclosed in U.S. Pat. No. 3,592,775.

Another process known in the art is the reaction of the corresponding acyloin for α-hydroxy oximes or the corresponding phenone for β-hydroxy oximes with a Raschig hydroxylamine in an alcohol medium under reflux conditions. An advantage of this method over the aforementioned methods is that the pH is adjusted by use of $NH_3$ instead of with the salt of a weak base, causing the effluent to be higher in ammonia but free of other materials.

Although any of the forementioned methods will produce an α-or β-hydroxy oxime compounds suitable for extracting metals from an ore solution, all suffer from the disadvantage of requiring relatively long time for their preparation. Frequently 18–22 hours are required, especially when the product oxime includes aromatic groups.

SUMMARY OF THE INVENTION

In accordance with the present invention, the time required to prepare α-and β-hydroxy oximes is substantially reduced by the addition of catalytic amounts of $Fe^{+2}$ and $Fe^{+3}$ contributing compounds. Non-limiting examples of preferred compounds include the water soluble ferric and ferrous salts preferably the ferric salts selected from the group consisting of ferric bromide, ferric lactate, ferric malate, ferric oxalate, ferric sulfate, ferric nitrate, ferric ammonium chloride, ferric ammonium fluoride, and ferric ammonium sulfate. More preferred is ferric ammonium sulfate.

DETAILED DESCRIPTION

The α-hydroxy oximes prepared by use of the presently claimed iron catalysts include, but are not limited to, the α-hydroxy oximes represented by the general formula:

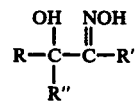

where R and R' are organic hydrocarbon radicals such as alkyl, aryl and alkylaryl radicals, and R" is hydrogen, alkyl, aryl and alkylaryl. Preferably R and R', and when applicable R", are unsaturated hydrocarbons containing 2 to 20 carbon atoms. Non-limiting examples of such α-hydroxy oximes include 7-n-butyl-7-hydroxydodecan-6-oxime, 6-ethyl-6-hydroxydecan-5-oxime, 6-n-butyl-6-hydrododecan-5-oxime, 7-n-pentyl-7-hydroxytridecan-6-oxime, 9-ethyl-7-n-pentyl-7-hydroxy-tridecan-6-oxime and 8-methyl-6-n-butyl-6-hydroxydecan-5-oxime. These oximes are more specifically set forth in U.S. Pat. Nos. 3,437,454 and 3,443,887.

β-hydroxy oximes which can be prepared by use of the presently disclosed iron catalysts, include those oximes represented by the general formula:

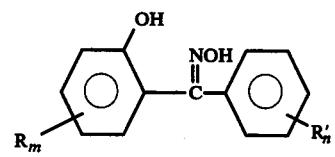

where R and R', may be independently saturated or ethylenically unsaturated aliphatic group and m and n are independently 0 or any whole number from 1 to 4. The total number of carbon atoms in $R_m$ and $R_n'$ is from 3 to 25. R and R' contain 1 to 25 carbon atoms when they are saturated aliphatic groups and 3 to 25 carbon atoms when they are ethylenically unsaturated groups. Non-limiting examples of such aromatic β-hydroxy oximes include 2-hydroxy-3'-methyl-5-ethylbenzophenoxime, 4-dodecyloxy-2-hydroxybenzophenoxime, and 2-hydroxy-5-nonyl-benzophenoxime. These oximes are more fully described in U.S. Pat. Nos. 3,592,775 and 3,925,472.

The iron compounds suitable for use in the present invention include those compounds capable of contributing a ferrous or ferric ion in an aqueous solution. Non-limiting examples of such compounds are the ferrous and ferric water soluble salts selected from the group consisting of ferric and ferrous bromides, ferrous acetate, ferric acid chloride and ferrous chloride, ferric and ferrous fluoride, ferric and ferrous nitrate, ferric and ferrous sulfate, ferric orthophosphate, ferric lactate, ferric malate, ferric oxalate, ferric and ferrous thiocyanate, ferric ammonium chloride, ferric ammonium fluoride and ferric ammonium sulfate. More preferred are the ferric salts of strong acids such as ferric chloride, nitrate, and sulfate. Most preferred is ferric ammonium sulfate, by which is meant any salt having ferric and ammonium cations and sulfate anions. It is also understood that iron metal can also be used owing to the fact that it also is capable of contributing limited amounts of iron ions in an aqueous solution.

Terms such as ferric or ferrous chlorides are used herein to include salts containing ferric or ferrous cations and chloride anions and, optionally, other cations which do not significantly detract from the catalytic activity. Preferred other cations are hydrogen cations and ammonium ions. The iron ion contributing compound will preferably be present in sufficient quantities to provide a ferric and/or ferrous ion concentration of between about 0.005% and about 0.1%, based on weight of ketone.

The process most preferred herein for preparing hydroxy oximes is that process which reacts the corresponding acyloin or phenone with a Raschig hydroxylamine solution (50% in excess) under reflux conditions in an alcohol medium, preferably methanol or ethanol. Owing to the use of a large excess of hydroxylamine, anhydrous ammonia is preferably used to adjust the pH of the reaction medium to about 6.8.

The term "Raschig hydroxylamine" as used herein means a solution obtained by the known Raschig method which typically is comprised of about 11 wt. % of $(H_2NOH)_2SO_4$ (4.46% $H_2NOH$), about 23 wt. % $(NH_4)_2SO_4$, about 7.5 wt. % $H_2SO_4$ and about 58.5% $H_2O$, wherein all weight percents are based on the total weight of the Raschig hydroxylamine solution.

Generally, because there is no practical way of removing the unreacted ketone, the reaction must be continued until the desired degree of oximation is achieved. Preferably, a maximum of only 2% of ketone or acyloin is left unreacted.

The method used to measure the degree of oximation can be direct gas chromatographic method which utilizes a 20 inch by ¼ inch. 0.5% carbowax 20M Glassport M column. Six minute post injection is used at 70° C. followed by a 15°/minute program to 240° C.

This invention may best be illustrated by the following non-limiting examples.

EXAMPLES 1–5

Preparation of 2-nonyl-5-hydroxybenzophenoxime

A series of runs was made at atmospheric presure wherein 0.15 mols of Raschig hydroxylamine and various quantities of ferric ammonium sulfate were added to a solution of 0.1 mols of 2-nonyl-5-hydroxy-benzophenone and 184 ml of methanol in a flask wherein the pH was adjusted to 6.8 with anhydrous $NH_3$. The flask, which contains a cresent stirrer and is fitted with a reflux condenser and thermometer is heated by a standard heating mantle to reflux temperature (depending on the alcohol used). A viscous slurry of a precipitated solid resulted in two liquid phases. On refluxing, the mixture quickly became more mobile as the finely divided solid phase became more granular. The reaction was continued to the desired extent as indicated by gas chromatographic analysis. The results are shown in the following table.

| Ketone moles | Amine moles | Methanol ml | $Fe_2(SO_4)_3$ $(NH_4)_2SO_4$ $24H_2O$ gm | % oximation reaction time in hours | | | | | | total reaction time hr. | % oxim. |
|---|---|---|---|---|---|---|---|---|---|---|---|
| | | | | 1 | 2 | 3 | 4 | 5 | 6 | | |
| 0.10 | 0.15 | 184 | 0 | | 25 | | | | | 19 | 90 |
| 0.10 | 0.15 | 184 | 0.025 | 25 | | 60 | | | 80 | 10.5 | 95 |
| 0.10 | 0.15 | 184 | 0.050 | 35 | | 70 | | | 90 | 10.5 | 98 |
| 0.10 | 0.15 | 184 | 0.100 | | | | | | 78 | 7 | 92 |
| 0.10 | 0.15 | 184 | 0.200 | | | | | | 87 | 7 | 94 |

The above table illustrates that the preparation of the hydroxy oximes can be substantially accelerated by the presence of ferric ions.

What is claimed is:

1. In a method for preparing hydroxy oximes which are α-hydroxy oximes or aromatic β-hydroxy oximes by reaction of hydroxylamine with a phenone or acyloin, the improvement which comprises conducting the reaction in the presence of a catalytic amount of an iron ion contributing compound selected from the group consisting of elemental iron and the soluble salts of iron.

2. The method of claim 1 wherein the iron ion contributing compound is an iron salt of a strong acid.

3. The method of claim 2 wherein the iron salt is selected from the group consisting of ferric and ferrous chlorides, ferric and ferrous phosphates, ferric and ferrous sulfates, and ferric and ferrous nitrates.

4. The method of claim 1 wherein the iron ion contributing compound is ferric ammonium sulfate.

5. The method of claim 1 wherein the α-hydroxy oxime is represented by the formula:

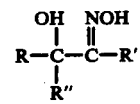

where R and R' are organic hydrocarbon radicals selected from the group consisting of alkyl, aryl and alkylaryl, and R" is selected from the group consisting of hydrogen, alkyl, aryl and alkylaryl.

6. The method of claim 5 wherein R, R' and R" together have 2 to 20 carbons.

7. The method of claim 1 wherein iron is present at a concentration of between about 0.005% and about 0.1%, based on weight of ketone.

8. In a method for preparing α-hydroxy oximes which comprises reacting the corresponding acyloin with a hydroxylamine salt under reflux conditions in an aliphatic alcohol medium wherein the reaction medium is neutralized with a weak base the improvement which comprises conducting the reaction in the presence of a catalytic amount of an iron ion contributing compound.

9. The method of claim 8 wherein the α-hydroxy oxime is represented by the formula:

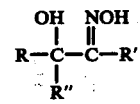

where R and R' are selected from the groups consisting of alkyl, aryl and alkylaryl, and R" is selected from the group consisting of hydrogen, alkyl, aryl and alkylaryl.

10. The method of claim 8 wherein the iron ion contributing compound is an iron salt of a strong acid.

11. The method of claim 10 wherein the iron salt is selected from the group consisting of ferric and ferrous chlorides, ferric and ferrous phosphates, ferric and ferrous nitrates, and ferric and ferrous sulfates.

12. The method of claim 8 wherein the iron ion contributing compound is ferric ammonium sulfate.

13. In a method of producing an oxime of the formula

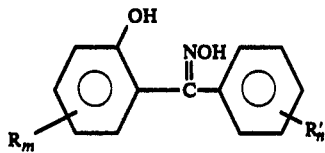

where R and R' are independently selected from the group consisting of alkanes having 1–25 carbons and ethylenically unsaturated alkanes having 3–25 carbons, m and n are independently 0–4 and $R_m$ and $R'_n$ together have 3–25 carbons, by reacting the corresponding phenone with hydroxylamine, the improvement which comprises conducting the reaction in the presence of a catalytic amount of an iron ion contributing compound selected from the group consisting of elemental iron and the soluble salts of iron.

14. The method of claim 13 wherein the oxime is 2-nonyl-5-hydroxy-benzophenone.

15. The method of claim 14 wherein the iron contributing compound is selected from the group consisting of ferric and ferrous chlorides, ferric and ferrous phosphates, ferric and ferrous nitrates, and ferric and ferrous sulfates.

16. The method of claim 14 wherein the iron contributing compound is ferric ammonium sulfate.

17. The method of claim 13 wherein the iron contributing compound is selected from the group consisting of ferric and ferrous chlorides, ferric and ferrous phosphates, ferric and ferrous nitrates, and ferric and ferrous sulfates.

18. The method of claim 13 wherein the iron contributing compound is ferric ammonium sulfate.

19. The method of claim 1 wherein said iron ion contributing compound is present in sufficient quantities to provide a concentration of between about 0.005% and about 0.1% ferric or ferrous ions based on weight of phenone or acyloin.

20. The method of claim 13 wherein said iron ion contributing compound is present in sufficient quantities to provide a concentration of between about 0.005% and about 0.1% ferric or ferrous ions based on weight of phenone.

* * * * *